United States Patent [19]

Nelson

[11] Patent Number: 5,716,272
[45] Date of Patent: Feb. 10, 1998

[54] MOISTURE/YIELD MONITOR GRAIN SIMULATOR

[75] Inventor: George F. Nelson, Coon Rapids, Minn.

[73] Assignee: New Holland North America, Inc., New Holland, Pa.

[21] Appl. No.: 744,217

[22] Filed: Nov. 5, 1996

[51] Int. Cl.$^6$ .................................................. A01E 12/00
[52] U.S. Cl. ........................... 460/7; 460/149; 56/10.2 R
[58] Field of Search .................................. 460/7, 4, 5, 6, 460/149, 150; 56/10.2 R, DIG. 15, DIG. 22; 324/664, 694; 364/400; 73/73, 74

[56] References Cited

U.S. PATENT DOCUMENTS 5,092,819  3/1992  Schroeder et al. ...................... 460/7

OTHER PUBLICATIONS

*IEEE Transactions on Instrumentation and Measurement*, vol. 41, No. 1, pp. 111–115, Feb. 1992.
Sensors, Sep. 1992, pp. 68–74.
Canadian Agricultural Engineering, vol. 34, No. 4, pp. 327–335 (1992).

*Primary Examiner*—Terry Lee Melius
*Attorney, Agent, or Firm*—Griffin, Butler, Whisenhunt & Kurtossy

[57] ABSTRACT

A monitor for measuring the moisture content of grain comprises an AC signal source for transmitting a measurement signal along a measurement signal path that includes a sensor region in which grain may, or may not, be present, and an analyzer for determining the attenuation of the measurement signal along the path, the analyzer producing an indication of the moisture content of grain in the sensor region that is dependent on the attenuation. A simulator is provided to permit calibration, testing, maintenance and/or demonstration of the monitor without the requirement of grain in the sensor region. The simulator includes a programmable attenuator that is selectively electrically inserted in the measurement signal path and a control circuit for controlling the attenuator so that the measurement signal is attenuated and the analyzer produces an indication of grain moisture content even though no grain is present in the sensor region. The attenuator may be a PIN diode or a programmable capacitor.

18 Claims, 2 Drawing Sheets

1

MOISTURE/YIELD MONITOR GRAIN SIMULATOR

RELATED APPLICATIONS

This application incorporates by reference my concurrently filed application Ser. No. 08/744,250 entitled Moisture/Yield Monitor Calibration On-The-Go.

FIELD OF THE INVENTION

The invention relates to a method and apparatus for simulating the presence or passage of grain in or through a monitor of the type used to measure the moisture content of grain and determine crop yield. The invention permits all elements of the monitor to be exercised for demonstration, test/maintenance or calibration purposes without requiring the presence of grain in the sensor region of the monitor.

BACKGROUND OF THE INVENTION

It is well known to provide grain harvesters with monitors for measuring the internal moisture content and bulk density of grain as it is harvested. In one type of monitor, transmit and receive antennas are disposed on opposite sides of a chute or tube through which the harvested grain flows. An RF microwave measurement signal is applied to the transmit antenna and the resulting signal at the receive antenna is analyzed to determine the attenuation and phase shift of the measurement signal. Knowing the phase shift and attenuation, the moisture content and bulk density of the grain may be calculated. Monitors of this type are described in IEEE Transactions On Instrumentation and Measurement, Vol. 41, No. 1, pgs. 111–115, February 1992; Sensors, September 1992, pgs. 68–74; and in my above-referenced application.

A second type of monitor, generally not as accurate as the microwave monitor, employs the variation in capacitance between two plates to determine the moisture content of grain between the plates. A system of this type is disclosed in U.S. Pat. No. 5,092,819.

Both types of monitors described above require the presence or passage of grain between the sensor electrodes (antennas or capacitor plates) in order to verify the performance of the monitors. This requirement makes it inconvenient to operate the monitors for test/maintenance, calibration and/or demonstration purposes, particularly when they are installed on harvesters. Even when used in a laboratory for experimental purposes as described in the above-cited IEEE publication it would be more convenient to be able to carry out experiments with the monitors without having to use grain in them.

SUMMARY OF THE INVENTION

An object of the invention is to provide a method and apparatus for simulating the presence of grain in the sensor region of a grain moisture monitor thereby permitting exercise of the monitor for maintenance/test, calibration or demonstration purposes without the presence of grain.

Another object of the invention is to provide a method of simulating the presence of grain in a sensor region of a grain moisture monitor having a signal source for transmitting a measurement signal along a measurement signal path through the sensor region and analyzer means for producing an indication of the moisture content of grain from attenuation of the measurement signal as it is transmitted along the path, the method comprising electrically inserting an attenuator into the measurement signal path and controlling the attenuator so as to attenuate the measurement signal to the same degree grain would attenuate the measurement signal if grain were present in the sensor region.

A further object of the invention is to provide a monitor for measuring the moisture content of grain, the monitor having a measurement signal path including a sensor region in which grain may selectively be present or not present, means for transmitting a measurement signal along the path through the sensor region, and an analyzer for producing an indication of grain moisture content of grain present in the sensor region, the circuit means being connected to the path and including means for determining the moisture content of grain present in the sensor region from the attenuation of the measurement signal in the path, the monitor being characterized in that it includes simulator means for simulating the presence in the sensor region of moist grain, whereby the transmitting means and the analyzer may be exercised to produce an indication of grain moisture content even though no grain is present in the sensor region.

The grain simulator is obtained by inserting a programmable attenuator into the measurement signal path to attenuate the measurement signal to the same degree that the moisture content of grain would attenuate the signal. The attenuator may be a PIN diode, preferably precisely calibrated to a known standard such as the National Institute of Standards and Technology, or it may be a calibrated programmable capacitor.

Other objects and advantages of the invention will become evident upon consideration of the following description and the accompanying drawings.

DESCRIPTION OF PREFERRED EMBODIMENTS

Figure 1:
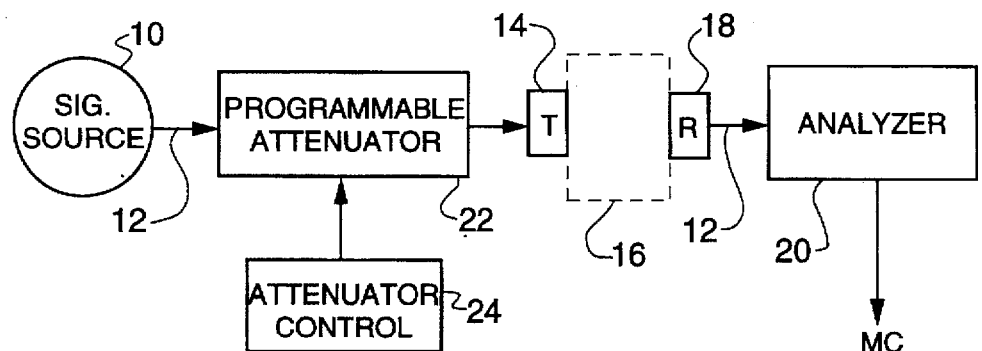
FIG. 1 schematically illustrates a moisture content monitor having a grain simulator therein.

FIG. 1 is a schematic diagram illustrating a grain simulator according to the invention in combination with a conventional monitor for measuring grain moisture content, the monitor being shown in generic form. The monitor includes an AC signal source 10 for transmitting a measurement signal along a measurement signal path 12 which includes a first sensor electrode 14, a sensor region 16 and a second sensor electrode 18.

The monitor may be a laboratory instrument for analysis of grain or it may be mounted on a grain harvester to measure the moisture content of grain as the grain is harvested. When used as a laboratory instrument, a container of grain is placed in sensor region 16. When the monitor is used on a harvester, the grain being harvested is pushed upwardly through the sensor region 16 by a broken flyte auger, as is known in the art.

As the measurement signal produced by signal source 10 is applied to electrode 14, it passes through the sensor region 16 and is attenuated and shifted in phase to a degree which depends on the moisture content and density of the grain. The attenuation is almost a straight line function of the moisture content. The attenuated and phase shifted measurement signal is sensed by the second electrode 18 and applied to an analyzer 20. Analyzer 20 analyzes the measurement signal to determine the attenuation (and possibly the phase shift) imposed on the measurement signal in traversing the measurement signal path, and produces a signal MC or other indication of the moisture content of the grain.

When there is no grain present in the sensor region 16, and assuming the monitor is properly calibrated, the indication of moisture content MC is always zero. Therefore, the entire monitor cannot be exercised for maintenance/test, calibration or demonstration purposes unless grain is available to fill the sensor region. This is inconvenient and wastes grain, particularly when the monitor is mounted in a harvester and the sensor region 16 comprises a grain feed tube within the harvester.

In accordance with the present invention, the monitor is provided with a simulator means for simulating the presence of grain in the sensor region 16 or the passage of grain through the sensor region. The simulator means comprises a programmable attenuator 22 for electrically inserting a known impedance into the measurement signal path 12 and an attenuation control means 24 for applying a control voltage to the attenuator to control the impedance. The attenuator is precisely calibrated to a standard hence it is possible to predict what the magnitude of the signal MC should be when a control voltage of known magnitude is applied to the attenuator.

The control means 24 includes circuit means for producing control signals of known magnitude for controlling the attenuator to thereby control attenuation of the measurement signal. When the monitor is performing its normal measurement function, the control means controls the attenuator 22 so that it does not attenuate the measurement signal in path 12. The analyzer 20 thus produces an output signal MC indicative of the moisture content of grain present in sensor region 16.

The attenuator 22 and attenuation control means 24 permit the monitor to be exercised for maintenance/test, calibration or demonstration purposes even though no grain is present in the sensor region 16. For example, a calibration check may be made on all components of the monitor, including the signal source 10, by applying a fixed magnitude control voltage of known magnitude to the attenuator 22 to cause an expected magnitude of the output signal MC, measuring the actual magnitude of the output signal, and determining how closely the actual magnitude matches the expected magnitude.

The monitor may be exercised for demonstration purposes by applying to attenuator 22 a control voltage of slowly varying magnitude while displaying the output signal MC. The output signal MC will slowly vary in magnitude thus simulating the changes in grain moisture content encountered when actually harvesting a crop.

The programmable attenuator 22, attenuation control circuit 24 an analyzer 20 may take any one of several forms as subsequently described. The programmable attenuator 22 may be located in the measurement signal path 12 downstream of the electrode 18 rather than upstream of the electrode 14.

Figure 2:
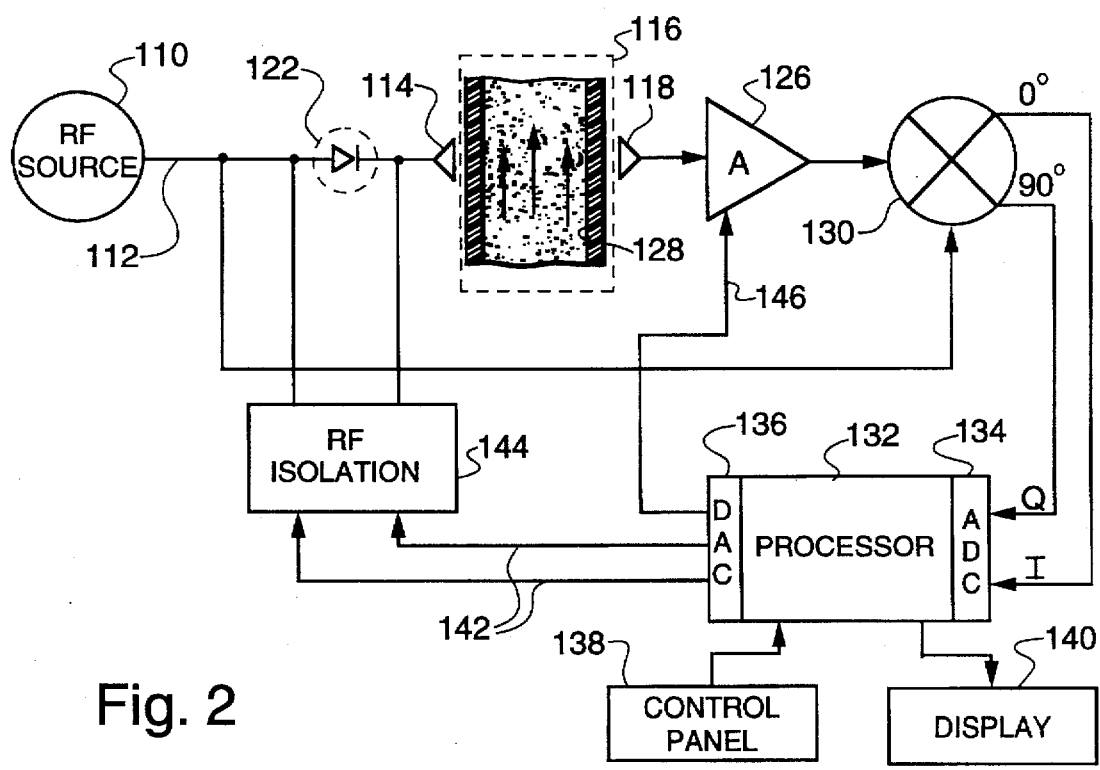
FIG. 2 illustrates a first embodiment of the invention adapted for use in a microwave monitor for measuring the moisture content of grain in a harvester; and, FIG. 3 illustrates a second embodiment of the invention adapted for use in a capacitive type monitor for measuring the moisture content of grain.

FIG. 2 illustrates a preferred embodiment of the grain simulator adapted for use with a conventional microwave type monitor for monitoring the moisture content of grain in a harvesting machine. The monitor comprises an RF source 110 for producing a measurement signal in the frequency range of about 1–10 gigahertz. The measurement signal is transmitted over a measurement signal path 112 that includes a programmable attenuator 122, a transmit antenna 114, a receive antenna 118 and a controllable gain amplifier or gain control means 126. The output of amplifier 126 is connected to one input of a quadrature demodulator 130 and the outputs of the demodulator are connected to a programmable computer or processor 132 through an analog to digital converter (ADC) 134.

Antennas 114 and 118 are sensor electrodes disposed on opposite sides of a sensor region 116. A grain feed tube 128 of the harvester extends through the sensor region and a broken flyte auger (not shown) pushes grain upwardly through tube 128 during crop harvesting. Tube 128 is made of a plastic or other material that is transparent to microwaves in the 1–10 GHz range, or is provided with windows of such a material, so that the measurement signal traversing path 112 is not affected by the tube.

The demodulator 130, processor 132 and ADC 134 comprise an analyzer for analyzing the measurement signal output from amplifier 126 and producing an output signal indicating the moisture content of grain flowing through tube 128. The measurement signal output from RF source 110 is applied as a reference signal to one input of demodulator 130 which compares the reference signal with the measurement signal output from amplifier 126 and produces two time varying output voltages I and Q, where I and Q represent the magnitude of the output signal from amplifier 126 measured at 0° and 90° of the reference signal. The voltages I and Q are converted to digital values by ADC 134 and processor 132 executes a stored program to first compute the attenuation A and phase shift $\phi$ imparted to the measurement signal as it traverses the measurement signal path 112. The attenuation $A=(I^2+Q^2)^{1/2}$ volts and the phase shift $\phi=\tan^{-1}$ (Q/I) degrees. The processor 132 then calculates the percent grain moisture content (wet basis) MC from the values A, $\phi$ and stored constant values, known in the prior art, which are specific for each type of grain (wheat, barley, etc) and each variety of grain of a given type (red winter, etc.). Reference may be made to my above mentioned concurrently filed application for an exemplary program executed by processor 132 to calculate, according to various experimentally developed equations known in the art, the moisture content of the grain moving through grain tube 128. A display 140 may be provided on an operator's console for displaying the moisture content of grain passing through tube 128.

For the purpose of simulating grain flow through the monitor, an attenuator 122 in the form of a programmable PIN diode is provided in the measurement signal path 112 at any point upstream of amplifier 126. The diode is calibrated to an accuracy traceable to the National Institute of Standards and Technology. Such diodes are commercially available from Hewlett-Packard Company. At RF frequencies, and with a forward bias voltage being applied, the diode acts as a pure resistance, the magnitude of the resistance being inversely proportional to the forward bias current. With reverse or zero bias the diode exhibits a very high resistance.

The processor 132 and a digital-to-analog converter (DAC) 136 comprise an attenuator control means for controlling the attenuator 122. The processor applies digital values one at a time to DAC 136 which converts each value to an analog bias voltage. The bias voltage is applied to the PIN diode attenuator 122 via leads 142 and an RF isolation circuit 144. The purpose of isolation circuit 144 is to isolate DAC 136 from the RF signal present on the measurement signal path 112.

The processor 132 is programmed to apply a high forward bias to the PIN diode attenuator 122 during normal harvesting operation. This causes the diode resistance to drop to practically zero, in effect electrically removing the diode from the measurement signal path so that the only attenuation of the measurement signal is that resulting from its passage through the grain.

To simulate the flow of grain through tube 128, say for test/maintenance or demonstration purposes, processor 132 accesses a stored table of digital values. These values may have been previously stored in a memory of the processor by operation of keys on an operator's control panel 138, or they may be values stored in a ROM in the processor. The digital values are chosen such that, when converted to bias voltages by DAC 136 and applied to PIN diode attenuator 122, the processor 132 will cause display 140 to display a time varying value of moisture content, just as it does when grain of varying moisture content is being harvested. The digital values are applied to DAC 136 to generate a time varying bias voltage that is applied to the PIN diode attenuator 122 to vary its resistance. As the attenuation of the measurement signal varies, demodulator 130 detects the variations and processor 132 computes values of moisture content which are successively displayed on display 140.

To simulate the flow of grain through the monitor for calibration purposes, the processor 132 applies a digital value to DAC 136 to cause a bias voltage of known value to be applied to PIN diode attenuator 122. The bias voltage causes the resistance of the attenuator to assume a known value simulating the attenuation imposed on the measurement signal by the moisture content of grain if grain was passing through tube 128. Demodulator 130 detects the attenuated measurement signal and processor 132 computes the simulated moisture content. Processor 132 then compares the computed simulated moisture content with a stored value representing the expected moisture content. If the computed moisture content is equal to the expected moisture content then the monitor is properly calibrated. If the computed moisture content and the expected moisture content are not equal, the processor generates a digital correction factor that is converted to an analog control voltage by DAC 136 and applied via lead 146 to the control input of the controllable gain amplifier 126.

In simulating the presence of grain, no phase shift is imposed on the measurement signal other than the inherent phase shift resulting from passage of the measurement signal over the path 112. This does not significantly alter the accuracy of the calibration or the simulation because moisture content is essentially a straight line function of attenuation. Phase shift, which is a function of grain density, has little effect in the calculation of moisture content.

Although the present invention provides for calibration of the monitor by simulating the presence of grain in the tube 128, the monitor shown in FIG. 2 may be calibrated on-the-fly. That is, the monitor may also be calibrated while harvesting is taking place and grain is flowing through the tube 128, as disclosed and claimed in my above-referenced copending application.

Figure 3:
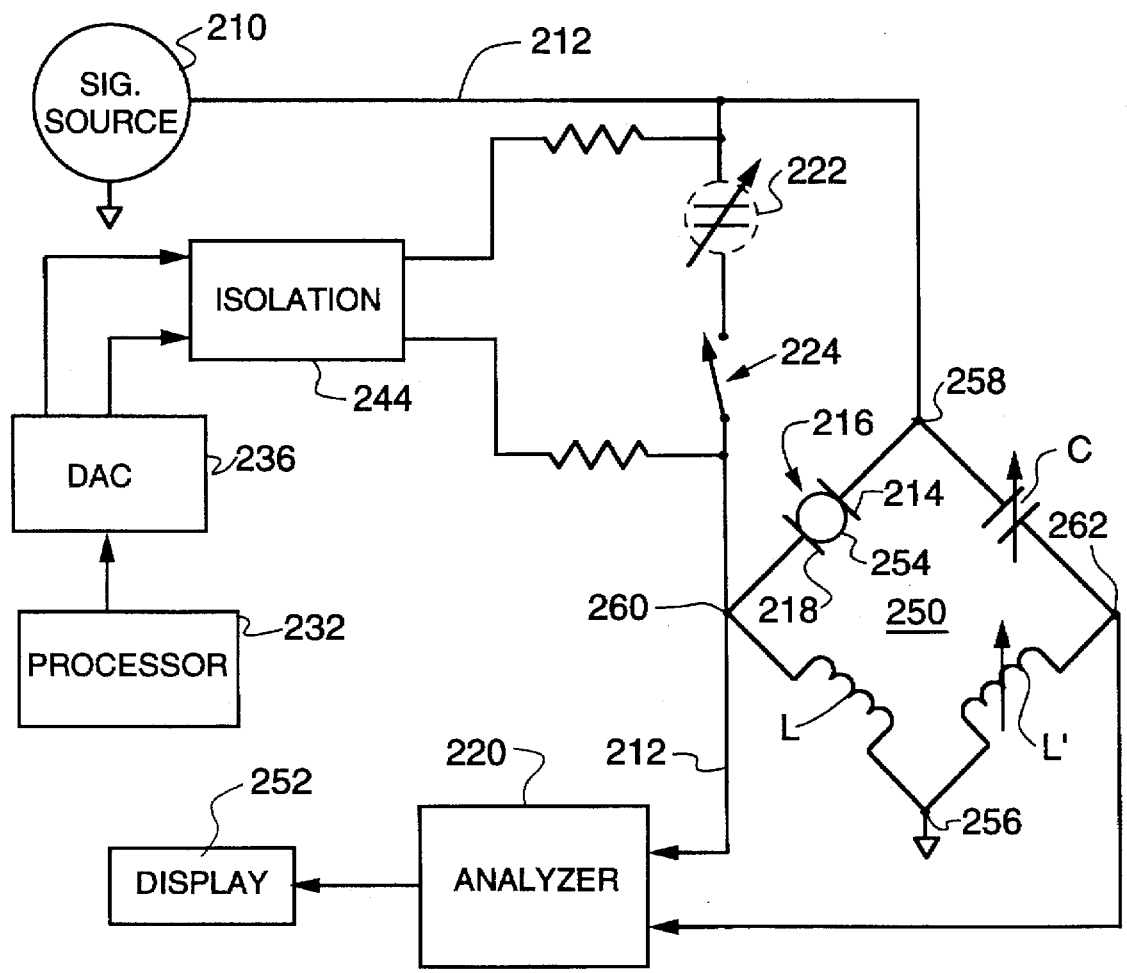

FIG. 3 illustrates the invention in the environment of a capacitance type monitor such as might be used in a laboratory, at a grain elevator, or even by a farmer. The monitor comprises a signal source 210 for generating a measurement signal, a bridge circuit 250, an analyzer 220 and a display 252.

Signal source 210 may be any AC source for generating a signal in the frequency range suitable for capacitance measurements and preferably generates a measurement signal in the low radio frequency range. One output of signal source 210 and an input node 256 of the bridge circuit are connected to ground and the second output of the signal source is transmitted via a measurement signal path 212 to input node 258 of the bridge circuit.

The bridge circuit 250 comprises first and second inductances L and L' and a capacitor C disposed in first, second and third legs, respectively. The fourth leg is provided with first and second sensor electrodes or plates 214 and 218 spaced apart to define a sensor region 216 for receiving a sample receptacle 254. The receptacle is made of a non-conductive material, preferably plastic, that is transparent to the measurement signal. The plates 214 and 218 and grain held in the receptacle 254 act as a variable capacitor having a capacitance determined by the particular grain in the receptacle and the grain moisture content. Capacitor C and inductance L' are preferably adjustable to permit balancing the bridge and remove any parasitic stray capacitance, thereby increasing the accuracy of grain moisture measurements.

The output nodes 260 and 262 of the bridge circuit are connected to inputs of the analyzer 220. The analyzer may be a known balance detector for determining the difference in magnitude between voltages present at nodes 260 and 262. The analyzer may be, for example, a Hewlett-Packard HP8510 network analyzer in which case the phase shift of the measurement signal may be determined in addition to its attenuation.

To determine the moisture content of a sample of grain, the bridge is first balanced with receptacle 254 empty. When properly balanced, the measurement signal applied to nodes 256 and 258 causes equal voltages to appear at nodes 260 and 262 and the analyzer output produces a zero output. After the bridge is balanced, the receptacle 254 is filled with the sample and positioned in the sensor region 216 between plates 214 and 218. The grain in receptacle 254 attenuates the measurement signal between nodes 258 and 260 but the voltage at node 262 remains unchanged. Analyzer 220 determines the difference in amplitude between the voltages at nodes 260 and 262 and applies an output signal representing this difference to display 252. The magnitude of this signal is almost a straight line function of the moisture content of the grain sample in receptacle 254 hence the display may be calibrated so as to indicate the percent moisture content of the grain.

The monitor is provided with a precisely calibrated programmable attenuator in the form of a variable capacitor 222 for simulating the presence of grain in the sensor region 216. Capacitor 222 is connected in series with a switch 224 between the output of measurement signal source 210 and bridge node 260. This places the switch and capacitor in parallel with the sensor region 216.

Capacitor 222 may be a silicon planar variable capacitance diode of the type sold commercially by Zetex Corp. Switch 224 may be a manually operated switch or a switch controlled from the processor 232 in which case it may be an electro-mechanical or electronic switch or even a PIN diode.

A control means for controlling capacitor 222 comprises a processor 232, which may be a conventional personal computer and a DAC 236 responsive to digital values applied thereto by the computer for generating analog control signals for controlling the capacitor. The control signals are applied to capacitor 222 through an isolation circuit 244 which isolates the DAC from the measurement signal produced by signal source 210.

The presence of grain in the sensor region 216 may be simulated by closing switch 224 and applying a digital signal to DAC 236 to produce a control voltage of known magnitude for controlling capacitor 222. This electrically inserts into measurement signal path 212 a known capacitance corresponding to the capacitance which would be introduced into the path by grain having a given moisture content.

When the receptacle 254 is empty, or is removed from sensor region 216, the sensor region acts as an open circuit hence the magnitude of the measurement signal at node 260 is dependent only on the attenuation introduced by capacitor 222. Analyzer 220 compares the voltages at nodes 260 and 262 and applies a signal corresponding to the difference in amplitude between the voltages to display 252 to indicate a moisture content. This moisture content is known or predictable from the value of the digital signal applied to DAC 236 hence calibration of the monitor may be checked.

The flow of grain of varying moisture content through sensor region 216 may be simulated by storing a table of values in the processor memory and applying them one at a time to DAC 236 so that capacitor 222 causes a varying attenuation of the measurement signal.

Although preferred embodiments have been described in detail to illustrate the principles of the invention, it will be understood that various modifications and substitutions may be made in the described embodiments without departing from the spirit and scope of the invention as defined by the appended claims.

I claim:

1. A monitor for measuring the moisture content of grain, the monitor having a measurement signal path including a sensor region in which gain may selectively be present or not present, means for transmitting a measurement signal along said path through said sensor region, said measurement signal being attenuated by moisture in grain present in said region, and an analyzer for producing from said measurement signal an indication of grain moisture content of grain present in said sensor region, said analyzer being connected to said path and including means for determining the moisture content of grain present in said sensor region from the attenuation of said measurement signal in said path, said monitor being characterized in that it includes simulator means for inserting into said measurement signal path an attenuation simulating an attenuation which would be caused by the presence of moist grain in said sensor region, whereby said transmitting means and said analyzer may be exercised to produce an indication of grain moisture content even though no grain is present in said sensor region.

2. A monitor as claimed in claim 1 wherein said simulator means comprises:

a variable attenuator electrically connected in said path so that said measurement signal flows through said attenuator; and, control means for controlling said attenuator.

3. A monitor as claimed in claim 2 wherein said attenuator is a PIN diode.

4. A monitor as claimed in claim 3 wherein said PIN diode is precisely attenuated to a known standard and said control means comprises means for applying a bias voltage of known magnitude to said PIN diode whereby the indication of moisture content produced by said analyzer is predictable.

5. A monitor as claimed in claim 3 wherein said control means comprises digital to analog converter means for selectively applying a bias signal of varying magnitude to said diode to vary the resistance of said diode, whereby said diode attenuates said measurement signal and said circuit means produces an indication of grain moisture content which varies as the magnitude of said bias signal varies.

6. A monitor as claimed in claim 5 wherein said control means further comprises a programmable processor having a memory for storing a table of values, each value corresponding to a different grain moisture content, said processor including means for applying said values from said table of values to said digital to analog converter means to produce said bias signal.

7. A monitor as claimed in claim 1 and comprising first and second electrodes connected in said measurement signal path and disposed on opposite sides of said sensor region.

8. A monitor as claimed in claim 7 wherein said first and second electrodes are a transmit antenna and a receive antenna, respectively and said signal source comprises means producing a measurement signal in the range of 1–10 gigahertz.

9. A monitor as claimed in claim 1 wherein said simulator means comprises:

a variable capacitance capacitor;

control means for controlling the capacitance of said capacitor; and switch means selectively electrically connecting said capacitor in parallel with said sensor region.

10. A monitor as claimed in claim 9 wherein said sensor region is defined by two electrodes spaced apart to provide a region for receiving grain, the moisture content of which is monitored.

11. A monitor as claimed in claim 10 wherein said electrodes and grain in said sensor region comprises a variable capacitor in one leg of a measurement bridge circuit.

12. A monitor as claimed in claim 1 wherein said sensor region comprises a flow path through which grain may move.

13. A monitor as claimed in claim 1 wherein said sensor region comprises part of a grain flow tube of a harvesting machine.

14. A monitor as claimed in claim 13 wherein said part of said grain flow tube is made of a material transparent to said measurement signal.

15. A monitor as claimed in claim 1 wherein said sensor region comprises a container made of a material transparent to said measurement signal.

16. A method of simulating the presence of grain in a sensor region of a grain moisture monitor having a signal source for transmitting a measurement signal along a measurement signal path through said sensor region, the measurement signal being attenuated by moisture present in the grain, and analyzer means for producing an indication of the moisture content of grain from attenuation of the measurement signal as it is transmitted along said path, said method comprising electrically inserting an attenuator into the measurement signal path and controlling the attenuator so as to attenuate the measurement signal and cause said analyzer to produce an indication of moisture content even though no grain is present in the sensor region.

17. A method as claimed in claim 16 wherein the attenuator is a precisely calibrated variable attenuator and the step of controlling the attenuator comprises applying a control voltage of variable magnitude to said attenuator whereby the analyzer means produces a time varying indication of moisture content simulating the passage of grain with a varying moisture content through the sensor region.

18. A method as claimed in claim 16 wherein the attenuator is a precisely calibrated attenuator and the step of controlling the attenuator comprises applying a control voltage of known magnitude to said attenuator to cause the analyzer means to produce a known magnitude indication of moisture content, whereby operation of said monitor may be checked and calibrated without grain in the sensor region.

* * * * *